(12) United States Patent
VanDusseldorp

(10) Patent No.: US 6,416,519 B1
(45) Date of Patent: Jul. 9, 2002

(54) SURGICAL EXTRACTION DEVICE

(76) Inventor: Gregg A. VanDusseldorp, 2177-A Green Valley Dr., Porter County, Crown Point, IN (US) 46307

( * ) Notice: Subject to any disclaimer, the term of this patent is extended or adjusted under 35 U.S.C. 154(b) by 0 days.

(21) Appl. No.: 09/714,808

(22) Filed: Nov. 15, 2000

Related U.S. Application Data

(60) Provisional application No. 60/165,624, filed on Nov. 15, 1999.

(51) Int. Cl.$^7$ .............................................. A61B 17/22
(52) U.S. Cl. ..................................................... 606/127
(58) Field of Search ................................ 606/127, 128, 606/114, 119–122, 124, 205–210

(56) References Cited

U.S. PATENT DOCUMENTS

| | | | | |
|---|---|---|---|---|
| 4,873,978 A | * | 10/1989 | Ginsburg | 606/127 |
| 5,281,230 A | * | 1/1994 | Heidmueller | 606/127 |
| 5,944,728 A | * | 8/1999 | Bates | 606/127 |
| 6,129,683 A | * | 10/2000 | Sutton et al. | 606/207 |

* cited by examiner

Primary Examiner—Kevin T. Truong
(74) Attorney, Agent, or Firm—Gary M. Hartman; Domenica N. S. Hartman

(57) ABSTRACT

An extraction device comprising a sheath, distal legs that project from the sheath, and actuating means for retracting the legs into the sheath and deploying the distal legs from the sheath. The distal legs are formed to have a parabolic curved shape, such that the distal legs automatically deploy radially outward and away from each other when deployed outside the sheath with the actuating means. As such, a plunger is not required to operate the legs. When retracted into the sheath with the actuating means, the distal legs elastically deform, collapsing radially toward each other to acquire a mid-deployed position in which the legs define a basket. The legs can be further retracted into the sheath, providing a stowed position in which the legs are substantially parallel to each other. Each of the distal legs has a concave cross-section that contributes greater strength to the legs, such that they maintain their form and alignment and provide greater grasping strength and expansion force than extraction devices of the prior art. As a result, the device is not only capable of moving, manipulating and extracting biological material, such as calculi and stones, but also man-made material such as implants and stents.

18 Claims, 2 Drawing Sheets

SURGICAL EXTRACTION DEVICE

CROSS REFERENCE TO RELATED APPLICATIONS

This application claims the benefit of U.S. Provisional Application No. 60/165,624, filed Nov. 15, 1999.

BACKGROUND OF THE INVENTION

1. Field of the Invention

The present invention provides an extraction device capable of capturing and releasing hard objects, and particularly for surgically moving, manipulating and extracting biological material and man-made material from the human body, such as required in ureteroscopic and renal stone extraction procedures.

2. Description of the Prior Art

Various instruments are known in the art for surgically removing stones and other hard materials from the body. An example is an instrument disclosed in U.S. Pat. No. 5,944,728 to Bates, which is incorporated herein by reference. Bates' instrument has arcuate legs that form a basket when a plunger is in a distal position, allowing the legs to radially collapse toward each other. The legs are actuated independently of the plunger with a cable, and may have cross-sectional shapes such as rectangular, round, D-shaped, or V-shaped. To expand the legs, the plunger must be actuated into engagement with the legs, forcing the legs radially apart from each other. As such, surgically moving, manipulating and extracting material from the human body is complicated by the requirement to additionally operate the plunger to expand and contract the legs.

BRIEF SUMMARY OF THE INVENTION

The present invention provides an extraction device that comprises a sheath, distal legs that project from the sheath, and actuating means for retracting the legs into the sheath and deploying the distal legs from the sheath. The distal legs are formed to have a parabolic curved shape, such that the distal legs automatically deploy radially outward and away from each other when deployed outside the sheath with the actuating means. As such, a plunger is not required to operate the legs. When retracted into the sheath with the actuating means, the distal legs elastically deform, collapsing radially toward each other to acquire a mid-deployed position in which the legs define a basket. The legs can be further retracted into the sheath, providing a stowed position in which the legs are elastically deformed to be substantially parallel to each other.

According to the invention, each of the distal legs has a concave cross-section that contributes greater strength to the legs while providing sufficient resiliency, such that the legs are able to maintain their form and alignment and provide greater grasping strength and expansion force than extraction devices of the prior art, while eliminating the requirement for a plunger or another additional component. As a result, the device is not only capable of moving, manipulating and extracting biological material, such as calculi and stones, but also man-made material such as implants and stents. The distal ends of the legs define jaws that are preferably angled outward so that an embedded material can be more readily extracted, such as a stone from the wall of the calyces in a kidney. An additional preferred feature of the invention is that the sheath is hollow to allow passage of irrigant or a laser fiber used to disintegrate biological materials. The sheath also may also include a hollow channel through which a sparking wire can be passed to enable the legs (if formed of a conductive material) to be energized with electrosurgical cutting or coagulating current.

Other objects and advantages of this invention will be better appreciated from the following detailed description.

DETAILED DESCRIPTION OF THE INVENTION

Figures 1, 2, 3:
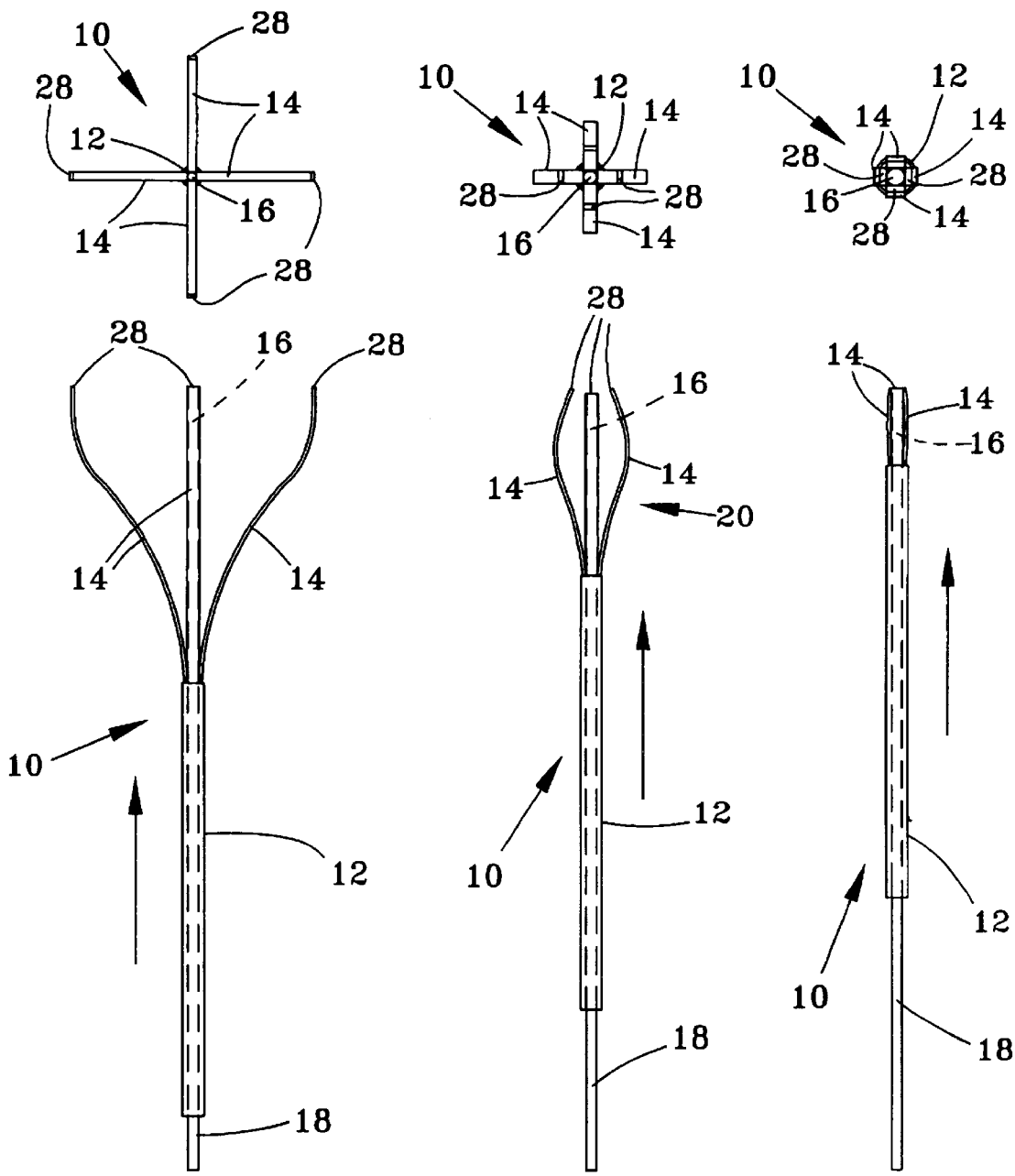
FIGS. 1 through 3 include side and end views of an extraction device in stowed, mid-deployment and deployed positions, respectively, in accordance with a preferred embodiment of this invention.

With reference to FIGS. 1 through 3, an extraction device 10 is shown in accordance with a preferred embodiment of this invention. The device 10 is particularly intended and suitable for ureteroscopic and renal stone extraction procedures, in which biological and/or man-made materials are required to be surgically moved, manipulated and/or extracted from the human body.

The extraction device 10 comprises a sheath 12, distal legs 14 that project from a passage within the sheath 12, and a cable 18 (or other suitable actuating member) for simultaneously retracting the legs 14 into the sheath 12 and deploying the legs 14 from the sheath 12. A distal end 16 of the cable 18 projects from the sheath 12 so as to be surrounded by the legs 14, as seen in FIGS. 1 through 3. The sheath 12 can be, formed of any suitable material known in the art. The passage within the sheath 12 is preferably sufficiently large to not only accommodate the legs 14 and cable 18, but also provide an irrigation or injection lumen, or a channel for a laser fiber, 32 (FIG. 6) to be passed through so that stones and other biological materials can be captured, held and fragmented to allow the resulting fragments to pass. The sheath 12 may also be equipped with a hollow channel (not shown) through which a sparking wire can be passed to enable the legs 14 (if formed of a conductive material) to be energized with electrosurgical cutting or coagulating current.

In a preferred embodiment, the device 10 is equipped with four distal legs 14, though it is foreseeable that fewer or greater numbers of legs could be employed. As seen in FIG. 3, each of the distal legs 14 is formed to have a parabolic curved shape, as by such known methods as stamping, rolling, extruding, etc. The legs 14 are formed from a sufficiently rigid material, such as a stainless steel, or a "shape memory" nickel-titanium alloy such as NITINOL, so that the legs 14 automatically deploy radially outward and away from each other (and away from the end 16 of the cable 18) when deployed outside the sheath 12 with the cable 18. As a result, and contrary to the prior art, the device 10 does not require a plunger capable of being actuated relative to the legs 14 in order to force the legs 14 radially apart. The legs 14 are sufficiently elastically deformable so that, when retracted into the sheath 12, the legs 14 elastically collapse radially toward each other to acquire a mid-deployed position (FIG. 2) in which the legs 14 define a basket 20. On further retraction into the sheath 12, the legs 14 are largely stowed within the sheath 12, with the distal ends of the legs 14 being substantially parallel to each other and to the end 16 of the cable 18.

A key feature of the present invention is that each distal leg 14 has a concave cross-section that contributes greater strength to the legs 14, such that the legs 14 maintain their form and alignment and provide greater grasping strength and expansion force than extraction devices of the prior art. As a result, the device 10 is not only capable of moving, manipulating and extracting biological material, such as calculi and stones, but also man-made material such as implants and stents. As depicted in FIG. 5, the legs 14 have a concave cross-section in the sense that the inward surfaces 22 of the legs 14 facing each other are concave, while the outward surfaces 24 of the legs 14 are convex. When fully collapsed, the legs 14 define a tubular shape in the sense that the legs 14 in combination generate a circular exterior cross-section and a circular opening 26. As more clearly seen in FIGS. 1–4 and 6, the distal ends of the legs 14 form jaws 28 whose terminal surfaces are preferably angled outward in the distal direction, so that embedded material can be more readily extracted, such as a stone embedded in the wall of the calyces in a kidney.

Figure 4A:
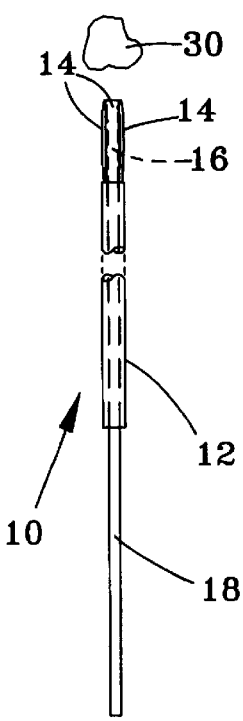
FIGS. 4A through 4C show the extraction device in the process of capturing a stone.
Figure 4B:
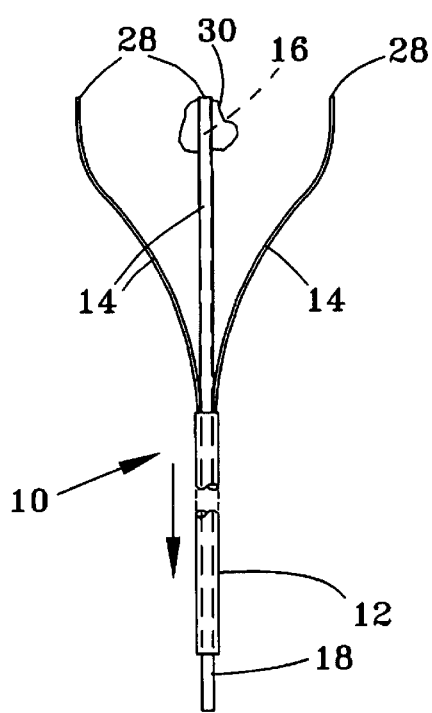
Figure 4C:
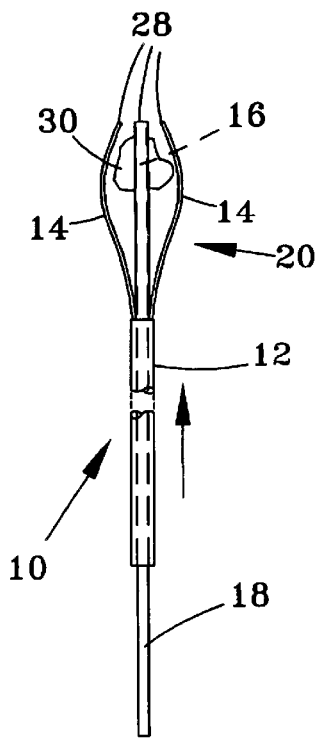
Figure 5:
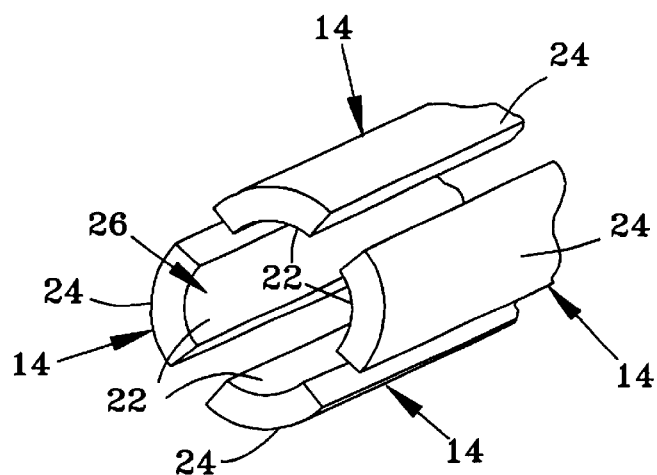
FIG. 5 is a perspective view of the end of the extraction device in a partially collapsed position, and illustrates the preferred concave geometry of the distal legs of the device.
Figure 6:
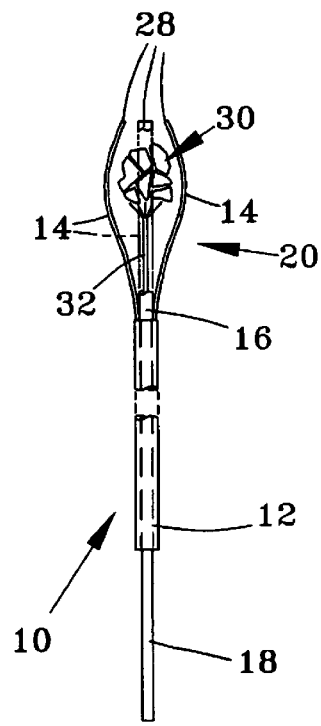
FIG. 6 represents a stone captured by the extraction device and in the process of being disintegrated with a laser beam.

FIGS. 4A through 4B illustrate the use of the extraction device 10 to remove a solid material 30, while FIG. 6 illustrates the additional use of a laser fiber 32 to disintegrate the material 30. As seen by contrasting FIGS. 4A and 4B, extending the legs 14 from the sheath 12 causes the legs 14 to be resiliently deployed outward to reacquire their parabolic curved shape. Once the material 30 is surrounded by the legs 14, the cable 18 is actuated to retract the legs 14, forming the basket 20 that grasps the material 30. By extending the legs 14 from the sheath 12, the material 30 can be released. As such, surgically moving, manipulating and extracting biological material and man-made material within the human body is greatly facilitated by the device 10 of this invention, particularly since these operations can be performed without additionally operating a plunger or other extraneous component to expand and contract the legs 14.

While the invention has been described in terms of a preferred embodiment, it is apparent that other forms could be adopted by one skilled in the art. For example, appropriate materials could be substituted for those noted. Accordingly, the scope of the invention is to be limited only by the following claims.

What is claimed is:

1. An extraction device comprising:
   a sheath having an interior passage;
   distal legs that project from the passage of the sheath, each of the distal legs having a parabolic curved shape, having a concave transverse cross-section, and being elastically deformable, the concave transverse cross-section of the distal legs being defined by each of the distal legs having an inward surface that is concave, and an outward surface that is convex; and
   actuating means for retracting the distal legs into the sheath, by which the distal legs are elastically deformed to retract into the sheath, and deploying the distal legs from the sheath, by which the distal legs elastically reacquire their parabolic curved shapes;
   wherein as a result of their parabolic curved shapes and their elastic deformability, the distal legs automatically deploy radially outward and away from each other when deployed outside the sheath with the actuating means, the extraction device lacking a second component to engage and force the distal legs away from each other.

2. An extraction device according to claim 1 wherein, as a result of their parabolic curved shapes, the distal legs elastically deform and collapse radially toward each other to acquire a mid-deployed position when retracted into the sheath with the actuating means.

3. An extraction device according to claim 2, wherein the distal legs define a basket in the mid-deployed position.

4. An extraction device according to claim 1 wherein, when further retracted into the sheath, the distal legs acquire a stowed position in which the distal legs are substantially parallel to each other.

5. An extraction device according to claim 4 wherein, when in the stowed position, the distal legs define a tubular shape having in combination a circular exterior cross-section and a circular opening.

6. An extraction device according to claim 1, wherein each of the distal legs has a distal end that defines a jaw having a terminal surface angled outward at an angle oblique to a longitudinal axis of the extraction device.

7. An extraction device according to claim 1, wherein the passage within the sheath is sufficiently large to accommodate the distal legs and the actuating means, and further to define a lumen.

8. An extraction device according to claim 1, further comprising a laser fiber disposed within the sheath.

9. An extraction device comprising:
   a sheath having an interior passage;
   distal legs that project from the passage of the sheath, each of the distal legs being elastically deformable and having a parabolic curved shape and a concave transverse cross-section; and
   actuating means for retracting the distal legs into the sheath, by which the distal legs are elastically deformed to retract into the sheath, and deploying the distal legs from the sheath, by which the distal legs elastically reacquire their parabolic curved shapes;
   wherein as a result of their parabolic curved shapes and their elastic deformability, the distal legs automatically deploy radially outward and away from each other when deployed outside the sheath with the actuating means without the assistance of a second component to engage and force the distal legs away from each other.

10. An extraction device according to claim 9 wherein, as a result of their parabolic curved shapes, the distal legs elastically deform and collapse radially toward each other to acquire a mid-deployed position when retracted into the sheath with the actuating means.

11. An extraction device according to claim 10, wherein the distal legs define a basket in the mid-deployed position.

12. An extraction device according to claim 9 wherein, when further retracted into the sheath, the distal legs acquire a stowed position in which the distal legs are substantially parallel to each other.

13. An extraction device according to claim 12 wherein, when in the stowed position, the distal legs define a tubular shape having in combination a circular exterior cross-section and a circular opening.

14. An extraction device according to claim 9, the concave transverse cross-section of the distal legs is defined by each of the distal legs having an inward surface that is concave, and an outward surface that is convex.

15. An extraction device according to claim 9, wherein each of the distal legs has a distal end that defines a jaw having a terminal surface angled outward at an angle oblique to a longitudinal axis of the extraction device.

16. An extraction device according to claim 9, wherein the passage within the sheath is sufficiently large to accommodate the distal legs and the actuating means, and further to define a lumen.

17. An extraction device comprising:

a sheath having an interior passage;

distal legs that project from the passage of the sheath, each of the distal legs having a parabolic curved shape and a transverse cross-section defined by an inward surface that is concave and an outward surface that is convex; and actuating means for retracting the distal legs into the sheath and deploying the distal legs from the sheath;

wherein as a result of their parabolic curved shapes the distal legs automatically deploy radially outward and away from each other when deployed outside the sheath with the actuating means without the assistance of a second component to engage and force the distal legs away from each other;

wherein as a result of their parabolic curved shapes the distal legs elastically deform and collapse radially toward each other to acquire a mid-deployed position when retracted into the sheath with the actuating means, the distal legs defining a basket in the mid-deployed position; and wherein when further retracted into the sheath, the distal legs acquire a stowed position in which the distal legs are substantially parallel to each other and define a tubular shape having in combination a circular exterior cross-section and a circular opening.

18. An extraction device according to claim 17, wherein each of the distal legs has a distal end that defines a jaw having a terminal surface angled outward at an angle oblique to a longitudinal axis of the extraction device.

* * * * *